US009345402B2

(12) United States Patent
Gao

(10) Patent No.: US 9,345,402 B2
(45) Date of Patent: May 24, 2016

(54) COMPACT EYE IMAGING AND EYE TRACKING APPARATUS

(71) Applicant: AUGMENTED VISION, INC., Tucson, AZ (US)

(72) Inventor: Chunyu Gao, Tucson, AZ (US)

(73) Assignee: Augmented Vision, Inc., Tucson, AZ (US)

( * ) Notice: Subject to any disclaimer, the term of this patent is extended or adjusted under 35 U.S.C. 154(b) by 0 days.

(21) Appl. No.: 14/023,299

(22) Filed: Sep. 10, 2013

(65) Prior Publication Data

US 2014/0071400 A1 Mar. 13, 2014

Related U.S. Application Data

(60) Provisional application No. 61/699,462, filed on Sep. 11, 2012, provisional application No. 61/736,832, filed on Dec. 13, 2012.

(51) Int. Cl.
| | |
|---|---|
| *A61B 3/14* | (2006.01) |
| *A61B 3/10* | (2006.01) |
| *G02B 27/14* | (2006.01) |
| *A61B 3/113* | (2006.01) |
| *G06K 9/00* | (2006.01) |

(52) U.S. Cl.
CPC ............ *A61B 3/113* (2013.01); *G06K 9/00604* (2013.01)

(58) Field of Classification Search
CPC ........... G02B 27/0172; G02B 27/0149; G02B 27/145; G02B 27/143; G02B 27/0025; G02B 27/144; G02B 27/013; G02B 23/02; G02B 23/18; G02B 5/045; G02B 27/0103; G02B 17/08; A61N 3/113; A61N 3/103; A61N 3/14; A61N 3/1225

USPC ........... 351/210, 41–176, 205, 206, 200, 211, 351/221; 359/630–639, 404, 407, 409, 410, 359/618, 619, 625, 13–14, 727, 732; 345/7–9; 631/633, 640; 340/438, 980, 340/995.1, 815.47, 815.74; 349/11; 348/115; 353/11–12, 28, 119
See application file for complete search history.

(56) References Cited

U.S. PATENT DOCUMENTS

| | | | |
|---|---|---|---|
| 4,109,263 | A | 8/1978 | Johnson |
| 4,917,457 | A | 4/1990 | Iizuka |
| 5,596,433 | A | 1/1997 | Konuma |
| 5,699,194 | A | 12/1997 | Takahashi |
| 5,701,202 | A | 12/1997 | Takahashi |

(Continued)

FOREIGN PATENT DOCUMENTS

WO 2010123934 A1 10/2010

OTHER PUBLICATIONS

D. Cheng, et al., "Design of an optical see-through head-mounted display with a low f-number and large field of view using a freeform prism," Applied Optics, 48(14), 2009.

(Continued)

*Primary Examiner* — Dawayne A Pinkney
(74) *Attorney, Agent, or Firm* — Michael Curley; Quarles & Brady, LLP

(57) ABSTRACT

An optical system for eye tracking is disclosed. The system includes a light guiding prism that guides light from an ocular object to an imaging system through multiple internal reflections. The light guiding prism may include one or more freeform surfaces having optical power.

12 Claims, 8 Drawing Sheets

(56) References Cited

U.S. PATENT DOCUMENTS

| | | | |
|---|---|---|---|
| 5,706,136 A | 1/1998 | Okuyama et al. | |
| 5,745,295 A | 4/1998 | Takahashi | |
| 5,790,306 A * | 8/1998 | Kleinberg et al. | 359/368 |
| 5,886,824 A | 3/1999 | Takahashi | |
| 5,909,317 A | 6/1999 | Nakaoka et al. | |
| 5,959,780 A | 9/1999 | Togino et al. | |
| 5,986,812 A | 11/1999 | Takahashi | |
| 6,023,373 A | 2/2000 | Inoguchi et al. | |
| 6,028,709 A | 2/2000 | Takahashi | |
| 6,034,823 A | 3/2000 | Togino | |
| 6,181,475 B1 | 1/2001 | Togino et al. | |
| 6,201,646 B1 | 3/2001 | Togino et al. | |
| 6,404,557 B2 | 6/2002 | Curley et al. | |
| 6,433,935 B2 | 8/2002 | Curley et al. | |
| 6,525,886 B1 | 2/2003 | Lewis | |
| 6,646,812 B2 | 11/2003 | Togino | |
| 6,653,989 B2 | 11/2003 | Nakanishi | |
| 6,735,328 B1 | 5/2004 | Helbing et al. | |
| 6,760,169 B2 | 7/2004 | Takahashi et al. | |
| 6,943,754 B2 | 9/2005 | Aughey et al. | |
| 6,977,776 B2 | 12/2005 | Volkenandt | |
| 7,414,791 B2 | 8/2008 | Urakawa et al. | |
| 7,542,210 B2 | 6/2009 | Chirieleison, Sr. | |
| 2001/0009478 A1 | 7/2001 | Yamazaki et al. | |
| 2002/0034016 A1 | 3/2002 | Inoguchi et al. | |
| 2003/0031216 A1 * | 2/2003 | Fallon | G03F 7/70025 372/29.01 |
| 2003/0107816 A1 | 6/2003 | Takagi et al. | |
| 2004/0085649 A1 | 5/2004 | Repetto et al. | |
| 2006/0072205 A1 | 4/2006 | Li et al. | |
| 2006/0215111 A1 * | 9/2006 | Mihashi | 351/205 |
| 2007/0064310 A1 | 3/2007 | Mukawa et al. | |
| 2008/0062537 A1 | 3/2008 | Liao | |
| 2009/0303317 A1 | 12/2009 | Tesar | |
| 2010/0171922 A1 | 7/2010 | Sessner et al. | |
| 2010/0220291 A1 | 9/2010 | Horning et al. | |
| 2011/0213664 A1 | 9/2011 | Osterhout et al. | |
| 2011/0214082 A1 | 9/2011 | Osterhout et al. | |
| 2011/0221656 A1 | 9/2011 | Haddick et al. | |
| 2011/0221657 A1 | 9/2011 | Haddick et al. | |
| 2011/0221658 A1 | 9/2011 | Haddick et al. | |
| 2011/0221659 A1 | 9/2011 | King, III et al. | |
| 2011/0221668 A1 | 9/2011 | Haddick et al. | |
| 2011/0221669 A1 | 9/2011 | Shams et al. | |
| 2011/0221670 A1 | 9/2011 | King, III et al. | |
| 2011/0221671 A1 | 9/2011 | King, III et al. | |
| 2011/0221672 A1 | 9/2011 | Osterhout et al. | |
| 2011/0221793 A1 | 9/2011 | King, III et al. | |
| 2011/0221896 A1 | 9/2011 | Haddick et al. | |
| 2011/0221897 A1 | 9/2011 | Haddick et al. | |
| 2011/0222745 A1 | 9/2011 | Osterhout et al. | |
| 2011/0225536 A1 | 9/2011 | Shams et al. | |
| 2011/0227812 A1 | 9/2011 | Haddick et al. | |
| 2011/0227813 A1 | 9/2011 | Haddick et al. | |
| 2011/0227820 A1 | 9/2011 | Haddick et al. | |
| 2011/0231757 A1 | 9/2011 | Haddick et al. | |
| 2012/0057129 A1 | 3/2012 | Durnell et al. | |
| 2012/0081800 A1 | 4/2012 | Cheng et al. | |
| 2012/0162549 A1 | 6/2012 | Gao et al. | |
| 2014/0071539 A1 | 3/2014 | Chunyu Gao | |

OTHER PUBLICATIONS

Rolland; Wide-angle, off-axis, see through head-mounted display; Optical Engineering vol. 39 No. 7; Jul. 2000 [retrieved on Apr. 20, 2012]; retrieved from the internet: ,URL:http://www.creol.ucf.edu/Research/Publications/1378.

Hua, et al.; A Polarized Head-Mounted Projective Display; Proceedings of the International Symposium on Mixed and Augmented Reality ISMAR'05, 2005 (retrieved on Apr. 20, 2012]; retrieved from internet: <URL:http://ieeexplore.ieee.org/stamp/stmap/jsp?tp=&arnumber=1544660>.

* cited by examiner

COMPACT EYE IMAGING AND EYE TRACKING APPARATUS

CROSS REFERENCE TO RELATED APPLICATIONS

This application claims priority to U.S. Provisional Patent Application No. 61/699,462, filed on Sep. 11, 2012 and U.S. Provisional Patent Application No. 61/736,832, filed on Dec. 13, 2012, the disclosures of which are incorporated herein by reference in their entirety.

FIELD OF THE INVENTION

The present invention relates generally to eye imaging and eye tracking devices, and more particularly, but not exclusively, to a compact eye-glass-like wearable optical device that is capable of capturing an eye image and tracking eye gaze direction.

BACKGROUND OF THE INVENTION

Eye tracking is the process to measure the eye movement or the eye-gaze direction. Various eye tracking technologies have been developed for use in a variety of applications, such as vision research, human computer interfaces, tele-surgery, product packaging, retail layout and advertising research, visual communication, and various military applications. One conventional method to track eye movement is to mount two cameras on a mount (e.g., a helmet), which capture images of each eye directly. This approach results in a bulky design and an unsightly appearance, which potentially may comprise research results.

In recent years, efforts have been made to design eye-glass like eye-tracking devices that are light, portable, ergonomic, and aesthetically more pleasing than previous technologies. For example, Tobii Technology of Stockholm, Sweden has developed an eye tracking system (www.tobii.com) that mounts the eye imaging camera on the arm of an eyeglass frame and captures an image of the eye through reflection off of the glass. The Tobii system has the advantage of an eye-glass like form factor, and is light weight, however, in order to properly capture the eye image through reflection off of glass, there must be sufficient clearance between the user's face and the glass surface to avoid the obstruction of the eye image by user's face or the imaging optics. This requires that very wide eyeglass lenses be used to avoid interference between the imaging path and any part of the user's face. The resulting overall package does not resemble a conventional pair of eyeglasses, and as a result, test subjects are unlikely to use the Tobii product outside of a laboratory environment.

Similarly, SensorMotoric Instruments GmbH or Teltow, Germany ("SMI") has developed an eye tracking system (www.smivision.com), which also has an eyeglass-like appearance and is lightweight. In the SMI system, the camera is mounted on the glass frame under the eye, and directly images the eye. This results in a thick and bulky frame design, which must move the camera far enough away from the face to avoid interference. Furthermore, in this system, the camera captures an eye image at a close distance and from a slanted direction (i.e., at a high angle), which results the eye image suffering keystone distortion. This arrangement also presents optical performance challenges due to the large depth of field necessary to accommodate all possible eye positions.

U.S. Pat. No. 6,735,328 discloses the use of a beamsplitter immersed in an eyeglass lens, off of which an eye is imaged by a vertically oriented camera positioned above a user's line of sight. While the arrangement of this patent is an improvement over other designs discussed above, the field of view of the camera in this arrangement is severely limited by the disclosed geometry.

U.S. Pat. No. 6,943,754 discloses an eye tracking system including a camera. The camera images an eye using a bulky and unsightly visor that hangs in front of the face of a user.

U.S. Patent Application No. 2010/0220291 discloses providing an array of optical detection elements directly onto an eyeglass-like lens located in front of an eye. While this device appears to be somewhat similar to a pair of eyeglasses in form factor, it is necessarily expensive and complex to fabricate, as it requires the use of semi-conductor fabrication processes to fabricate optical detectors and their associated electronics on a curved glass lens substrate.

SUMMARY OF THE INVENTION

The present invention concerns an optical apparatus that is capable of capturing eye image and tracking eye gaze direction. The present invention aims to provide an eye imaging and gaze tracking device that is compact and lightweight, has an eye-glass appearance and is wearable like a pair of ordinary eyeglass. The present invention also offers see-through capability which provides to the observer the capability of viewing the surrounding environment through the glass with minimum distortion and superior optical quality.

Embodiments of the invention are directed to using a thin prism between an eye and a camera system. The thin prism acts as a light-guide, which folds the imaging path between the camera and the eye. The thin prism also optionally folds an illumination path between an illumination source and the eye, thereby providing on-axis illumination. This arrangement enables a thin, eyeglass like eye tracking device, which captures a frontal (i.e., on-axis) or near frontal image of the eye at a distance while maintaining a light-weight, visually appealing form factor.

Other embodiments of the invention use a corrective optical element to eliminate any deviation or aberrations in the see-though viewing path introduced by the thin prism, such that a user of the device can comfortably see through the eye-tracker as normal. For example, in one of it aspects, the invention may include a wedge prism having only planar surfaces. This prism acts as a light guide to supply illumination light to the eye, as well as proving imaging light to the camera from the illuminated eye. In this embodiment, the invention includes a complementary prism, which is arranged with respect to the thin prism such that the two prisms appear to the eye as a plane-parallel plate, or other weakly powered optic.

In alternative embodiments, an eye-tracker according to the invention uses a free-form prism between the eye and a sensor. The freeform prism includes one or more surfaces with optical power, which are used both for imaging of the eye onto the sensor, and for optical aberration control. In certain embodiments, the freeform prism is used in conjunction with, or exclusive of, additional focusing optics such as a camera outside of the prism.

In one embodiment, the invention is directed to an optical system for eye tracking. The system has a prism with a first, second and third surface, and a first optical axis intersecting the first surface. The prism also has a second optical axis that intersects, and is approximately orthogonal to the third surface. The system also includes an imaging system and a sensor arranged along the second optical axis. The prism is configured such that an ocular object positioned about the first optical axis is imaged by the imaging system onto the sensor through the prism.

In another embodiment, the prism is configured such that light from an ocular object positioned about the first optical axis enters the prism at the first surface and exits the prism through the third surface prior to being imaged by the imaging system onto the sensor.

In another embodiment, the prism is configured such that light from an ocular object positioned about the first optical axis reflects off an interior side of the second surface prior to exiting the prism through the third surface. In yet another embodiment, the prism is configured such that light propagating along the first optical axis that enters the prism at the first surface and reflects at least twice within the prism to exit the third surface along the second optical axis.

In some embodiments, the prism is configured such that light from an ocular object positioned about the first optical axis entering the prism along the first axis reflects off an interior side of the second surface and reflects off an interior side of the first surface before exiting the prism through the third surface. In other embodiments, the prism is configured such that the reflection off the interior side of the first surface occurs by total internal reflection.

In certain embodiments, the prism is configured such that light from an ocular object positioned about the first optical axis entering the prism along the first axis reflects off an interior side of the second surface, reflects off an interior side of the first surface, and again reflects off an interior side of the second surface before exiting the prism through the third surface.

In some embodiments, the first surface of the prism includes a highly reflective coating for light within a predetermined wavelength range incident on the interior side of the first surface. In some embodiments, the reflective coating extends over only a portion of the first surface. The reflective coating, in some embodiments, comprises a dielectric thin film stack capable of high reflectivity for near infrared light.

In certain embodiments, the second surface of the prism has a coating having high reflectivity for light within a predetermined wavelength range incident on the interior side of the second surface. In some embodiments, the predetermined wavelength range is between about 700 nm and 1.5 um. In certain embodiments, the high reflectivity coating is a dielectric thin film stack having of high reflectivity for near infrared light.

In certain embodiments, the imaging system of the system has a first lens, a second lens, and a stop located between the first and second lenses. In alternate embodiments, at least one of the first, second or third surfaces is a freeform surface. In some embodiments, at least one of the first, second or third surfaces has optical power.

Some embodiments include a corrective optical element arranged along the first optical axis, wherein the corrective optical element has a first surface adjacent to the second surface of the prism, and a second surface, and wherein the corrective optical element is arranged such that its second surface is approximately parallel to the first surface of the prism. Alternative embodiments of the system include a corrective optical element arranged along the first optical axis, wherein the corrective optical element has a first surface adjacent to the second surface of the prism, and a second surface, and wherein the corrective optical element is arranged such the corrective optical element counteracts any visual distortion introduced by the prism when looking through the prism and the corrective optical element along the first optical axis.

In some embodiments, the optical system has at least one light source arranged to illuminate an ocular object located about the first optical axis. In some embodiments, the light source comprises an infrared light emitting diode. In certain embodiments, the light source is arranged to direct light along the second optical axis into the third surface, while in others, the light source is arranged to directly illuminate an ocular object without passing through the prism.

Other embodiments include a mount to position the prism, the imaging system and sensor a predetermined distance from an ocular object of a subject, and to align the ocular object to the first optical axis.

In other embodiments, the invention includes an eye tracking system with an optical sensor, an imaging system, and a prism. The prism has a first, second and third surface. The prism also has a first optical axis approximately orthogonal to the first surface, and a second optical axis approximately orthogonal to the third surface. The prism is configured to reflect light from an ocular object located about the first optical axis off of an interior side of the second surface through the third surface, such the ocular object is imaged by the imaging system on the optical sensor. The system also includes a programmable computer processor in electronic communication with the optical sensor, and a non-transitory computer readable medium in electronic communication with the programmable computer processor, the non-transitory computer readable medium having computer executable instructions encoded thereon to cause the programmable processor to recognize the position of an ocular object located along the first optical axis.

In some embodiments, the prism is configured such that light entering the prism along the first axis reflects off an interior side of the second surface and reflects off an interior side of the first surface before exiting the prism through the third surface. Other embodiments have a corrective optical element arranged along the first optical axis, wherein the corrective optical element arranged such the corrective optical element counteracts any visual distortion introduced by the prism when looking through the prism and the corrective optical element along the first optical axis.

In some embodiments, the invention is directed to an optical system for eye tracking. The system includes an optical sensor, an imaging system, and a prism with a first, second and third surface. The prism is arranged such that light entering the prism from an ocular object undergoes multiple reflections within the prism prior to exiting the prism to be focused by the imaging system. The system also has a light source for illuminating an ocular object to be imaged by the imaging system.

Embodiments of the invention have certain advantages, in particular, over the conventional systems referenced above. For example, by placing a dense optical medium (e.g., the material of the prism) in object space between the camera and the eye, the system takes advantage of the optical phenomenon of reduced distance by increasing the physical distance (along the folded optical path through the prism) between the camera and the eye. This increased physical path length "pushes" the camera a farther distance off of the optical axis of the eye as compared to the location it would occupy if the path between the eye and the camera were in air, and that path was folded, for example, with a simple air-immersed fold mirror or beamsplitter. The consequence of this is that the camera can be located well out of the normal clear aperture of a conventional pair of eyeglass lenses, and does not therefore interfere with the subject's normal field of view. Yet at the same time, the eye is imaged by the camera from an on-axis position.

Additionally, the use of a light guiding prism enables eye tracking over a greater field of view than with conventional devices. By using a light guiding prism, a first reflective surface inclined at a relatively small angle with respect to the eye's optical axis (e.g., approximately 27.5 degrees, measured from the surface normal of the reflective surface) can be used to fold light from a wide range of field positions. This allows the eye to be tracked over a wider range of positions as compared with, for example, the single fold arrangement described above with respect to U.S. Pat. No. 6,735,328.

Additionally, eye tracking devices according to embodiments of the invention can be realized with very thin prisms by folding the optical path inside the prism, 5 mm or less, which is not unreasonably thick as compared to a conventional pair of eyeglasses. While certain embodiments use total internal reflection to accomplish at least one reflection within the light guiding prism, other embodiments use "hot mirrors" or reflective coatings that are reflective in the infrared while being transmissive in the visible spectrum to guide the imaging light up and away from the eye's optical axis. The use of infrared reflective coatings eliminates the TIR requirement on certain reflections for achieving high reflective efficiency, thereby allowing the prism to use a small reflection angle. This results in the prism being thinner than would be the case if a TIR condition was required. Furthermore, these coatings do not interfere with the subject's ability to see real-world scenes through the prism because imaging of the eye is done in the infrared, and the coatings are invisible in the visible spectrum.

Additionally, certain embodiments of the invention use freeform, rather than planar prisms. Such prisms may have deterministic, aspheric, non-rotationally symmetric surfaces with optical power, which enables the prism to be used for focusing power and/or aberration control.

Additionally, by mating a guiding prism in the eye imaging path with a complementary and corrective optical element, the subject's view of real-world scenes is unobstructed and aberration free.

These and other features, aspects, and advantages of the present invention will become better understood upon consideration of the following detailed description and drawings.

BRIEF DESCRIPTION OF THE DRAWINGS

Implementations of the invention will become more apparent from the detailed description set forth below when taken in conjunction with the drawings, in which like elements bear like reference numerals.

DETAILED DESCRIPTION OF THE INVENTION

The invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
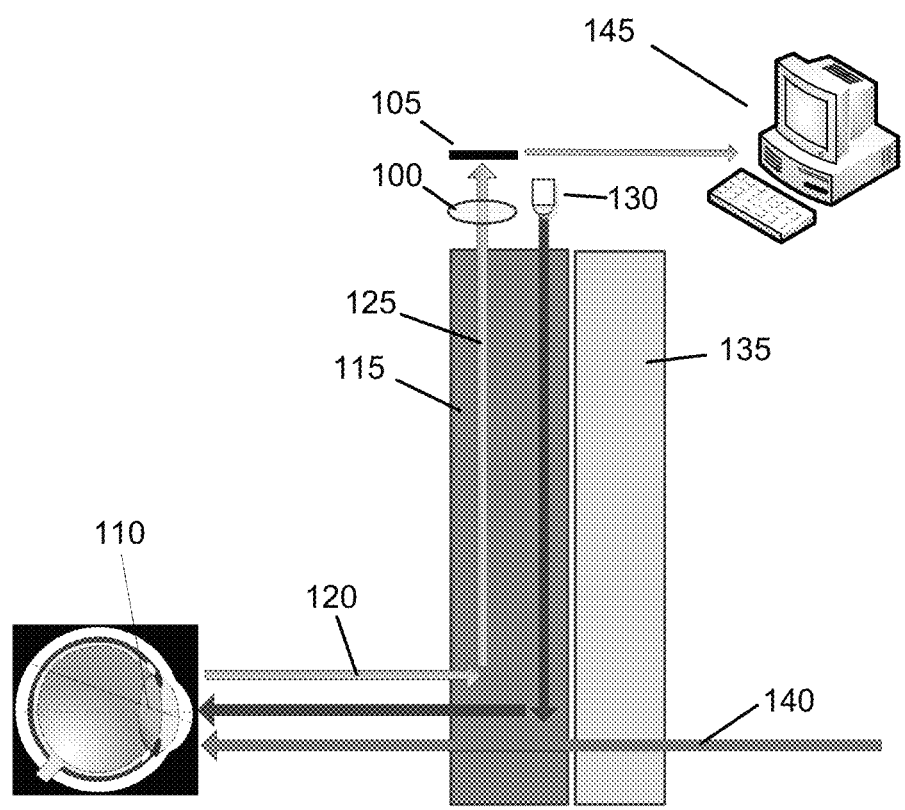
FIG. 1 is a schematic block diagram of an eye tracking system according to an embodiment of the invention.

FIG. 1 is a schematic block diagram of an eye tracking system according to an embodiment of the invention. In the system of FIG. 1, an imaging system 100 is provided, represented by a lens. Imaging system 100 images an ocular object located at eye 110 onto an optical sensor 105. Optical sensor 105 can be any device that translates optical power into electric signal, for example, a CMOS or CCD array. In accordance with the embodiment of FIG. 1, imaging system 100 images the ocular object onto sensor 105 through a prism 115. Prism 115 has at least two optical axes: a first optical axis 120, along which light from the ocular object enters prism 115, and a second optical axis 125 along which light from the ocular object exits prism 115 before being focused onto sensor 105 by imaging system 100.

The system of FIG. 1 also includes an illumination source 130, for example, a light emitting diode ("LED"). The LED is located adjacent to or otherwise in close proximity to imaging system 100 such that it delivers light along or parallel to the imaging optical axes 120, 125, but in a counter propagation direction. In other words, illumination source 130 sends illumination light down the same or a similar path through prism 115 to eye 110 that light from eye 110 takes on its way to imaging system 100.

The system of FIG. 1 also includes corrective optical element 135. Corrective optical element 135 compensates for optical aberrations, wedge, and other optical artifacts introduced by prism 115 when a subject looks through prism 115. In other words, corrective optical element 135 is configured to allow for light propagating to a subject's eye along a viewing path 140, to reach the eye without obscuring or otherwise distorting the view of a subject through both optical elements 115, 135. For example, in the event that prism 115 presents a wedge to a subject along a viewing path 140, corrective optical element 135 is configured as a wedge oriented 180 degrees about viewing path 140 such that, together, elements 115 and 135 form a plane parallel plate, or some other non-distorting optical element, along viewing path 140.

The system of FIG. 1 also includes a computer 145 in electronic communication with sensor 105 and non-illustrated non-transitory computer readable medium (e.g., a hard disk drive). Computer 145 receives electronic information (i.e., image data) from sensor 105 regarding the levels of optical power on the pixels of sensor 105, and applies an eye-tracking algorithm to determine the location of an ocular object within the field of view of the sensor 105.

Figure 2:
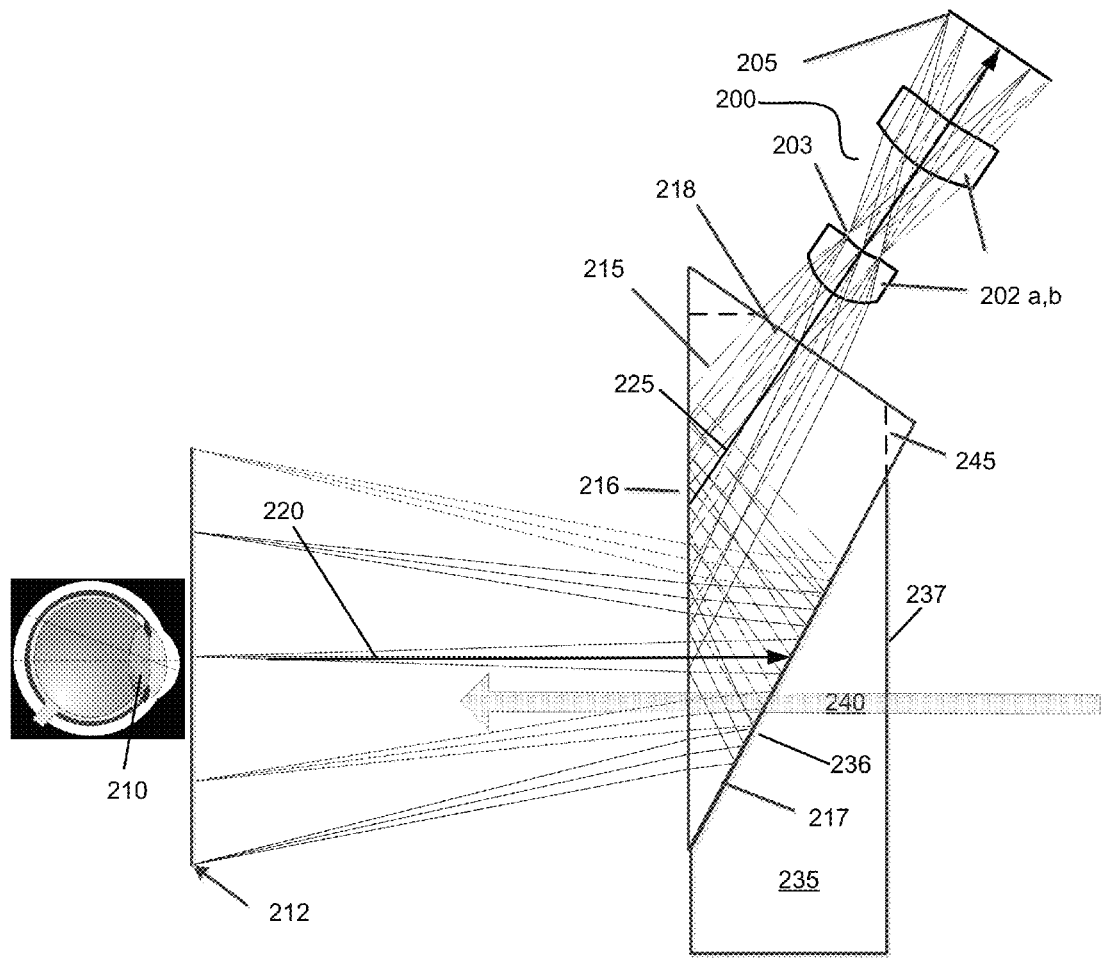
FIG. 2 is a schematic illustration of an eye tracking system according to an embodiment of the invention using a planar prism and an optional corrective optical element.

FIG. 2 shows an embodiment of a system for eye tracking according to another embodiment of the invention. In the embodiment of FIG. 2, an imaging system 200 is provided comprising a plurality of lenses (i.e., a first and second lens 202 a, b), having an aperture stop 203 located between the two. In one embodiment, the stop 203 is located at a second surface of first lens 202a. The system of FIG. 2 also includes an optical sensor 205, on which imaging system 200 forms an image of an ocular object from an eye 210. Additional lenses may be included in imaging system 200 as desired, e.g., for aberration control.

The system of FIG. 2 includes optical sensor 205. Optical sensor 205 can be any device that translates optical power into electric signal, for example, a CMOS or CCD detector array. Together, imaging system 200 and sensor 205 may be provided (and referred to herein) as a camera.

The system of FIG. 2 includes a prism 215, which has three planar surfaces, a first surface 216, a second surface 217 and a third surface 218. Prism 215, imaging system 200 and sensor 205 are arranged and configured such that an ocular object located within a predetermined field of the view defined by the imaging system 200 and the sensor 205, is imaged through prism 215 onto sensor 205. The optical system has a first optical axis 220, along which light from the eye 210 located at objective plane 212 propagates as it enters prism 215 at its first surface 216. The first optical axis 220 is approximately orthogonal to the first surface 216 of the prism 215. The optical system also has a second optical axis 225, which is approximately orthogonal to the third surface 218 of prism 215. The imaging system 200 and the sensor 205 are arranged along the second optical axis 225.

The optical system of FIG. 2 is optionally rigidly held in a pre-determined position with respect to a subject's eye, i.e., with a non-illustrated mounting system. The mounting system may include a head-mounted apparatus similar to a pair of conventional spectacles. The imaging system 200 has a field of view defined by imaging system 200 and sensor 205. In one embodiment, the imaging system 200 has an effective focal length 7.5 mm and the sensor 205 has an active area of 5.7 mm×4.3 mm, which provides a field of view of 41.6°×32° and covers an area of 20 mm×15 mm at object plane 212 positioned at 18 mm from first surface 216.

In operation, an ocular object located in or on eye 210 is illuminated with a non-illustrated illumination source. Preferred illumination sources include light emitting diodes ("LEDs"), emitting in the near infrared, and an integrated focusing lens, such are used in standard T3 or T5 LED packages. As used herein, "near infrared" means light in the wavelength range of between 700 nm and 1.5 um. In some embodiments, the preferred illumination wavelength is 850 nm. Exemplary arrangements for illuminating eye 210 are set forth in additional detail below with respect to FIG. 7.

Illumination light reflects off an ocular object located in proximity to eye 210. In some embodiments, the eye pupil is the ocular object imaged. In other embodiments, the first Purkinje image, which is the virtual image formed by the reflection of a point source off the anterior surface of the cornea is used. Any physical or optical object associated with the eye that can be uniquely identified and that will indicate ocular position, pupil position, or gaze direction is an acceptable ocular object that may be imaged and tracked within the scope of the invention.

Upon illumination of the ocular object, light propagates along a first optical axis 220. First optical axis 220 is established by the design parameters of prism 215 and imaging system 200 as the optical axis of imaging system 200 in object space before it is folded and translated via reflection and refraction through prism 215. A non-illustrated mounting system mounts the eye-tracker of FIG. 2 (or enforces the position of a subject's head) such that eye 210 is placed on or about first optical axis 220 at or near objective plane 212. The field of view of the eye tracker, which is a function of sensor 205 and imaging system 200 is sufficient to image the ocular object of interest throughout a variety of field positions located about axis 220. In one embodiment, this field of view, or imaged eye area measures 20 mm (horizontal) by 15 mm (vertical) for a sensor measuring 5.7 mm×4.3 mm.

Light from the illuminated ocular object enters prism 215 at prism 215's first surface 216. In the embodiment of FIG. 2, first surface 216 is approximately orthogonal to first optical axis 220, but this is not a requirement. After entering prism 215 and refracting at first surface 216, light from the ocular object reflects at an interior side of prism 215's second surface 217. Second surface 217 makes an angle with first surface 216, which in a preferred embodiments is 27.5 degrees. Second surface 217 has disposed thereon a highly reflective coating optimized for high reflection at the illumination wavelength. The highly reflective coating on second surface 217 is also optimized to be highly reflective at the relevant angles, i.e., at the incidence and reflectance angles for light received by the surface from the ocular object and reflected from the surface, as well as for light received along an illumination path, which encounters second surface 217 at the same angles. In the embodiment of FIG. 2, the highly reflective coating of surface 217 is capable of high reflectivity in the near infrared, and in particular, at the designated wavelength of 850 nm and over a range of angles between about 18° and 38°. The coating also has low or zero reflectivity in visible spectrum (400 nm~700 nm). In a preferred embodiment, highly reflective coating is a dielectric thin-film stack designed for use on an acrylic-air interface at the wavelengths and over the angles referenced above. In other embodiments, the highly reflective surface is designed for immersion in acrylic. The design of highly reflective surface may be performed according to conventional thin-film design methods.

Upon reflection from the highly reflective second surface 217, light from the ocular structure propagates back through prism 215 to reflect off of an interior side of first surface 216. In the embodiment of FIG. 2, the angle between first and second surfaces 216, 217 is chosen such that all rays in the imaging ray bundle for all field points intersect an interior side of the first surface 216 above the critical angle, such that the illustrated reflection off of first surface 216 occurs by total internal reflection ("TIR"). This condition, however, is not a requirement. In other embodiments, a region of first surface 216 (e.g., a region of the surface closer to imaging system 200) includes a highly reflective coating similar to the coating on second surface 217. As can be seen from FIG. 2, rays intersecting an interior side of first surface 216 in the region of that surface closer to axis 220 do so at large angles (measured with respect to the surface normal). As one travels vertically up surface 216 in the direction of camera 200, it is apparent that the reflections occur at increasingly small angles. If, at some point, these incident angles become too small to support TIR, the portion of first surface 216 over which the rays would refract out of prism 215 can be coated with an infrared highly reflective coating.

Upon reflection from first surface, light from the ocular structure propagates still through prism 215 along a second optical axis 225 until encountering third surface 218, whereupon, the imaging light exits prism 215 and refraction occurs. At this point, the light is collected by imaging system 200 and focused onto sensor 205. Second optical axis 225 is the optical axis of imaging system 200, or is the axis of rotational symmetry for lenses 202a, b.

As can be seen from FIG. 2, in the event that prism 215 is fabricated using a traditional cut-and-polish process (e.g., in the event that it is fabricated in glass), superfluous regions 245 may be created. These may occur in the corners, in particular. In certain embodiments, weight is saved by cutting off these unnecessary regions with corner cuts. In the event that prism 215 is molded or cast in a polymer material, prism 215 may be fabricated using the minimum possible material, without the inclusion of superfluous regions 245.

In a preferred embodiment, the eye tracking system of FIG. 2 is mounted to a subject's head, for example, in a form-factor similar in size, weight and appearance to conventional eyeglasses. Such a form factor is useful when conducting real-world testing and data-gathering, since oftentimes, the goal of eye tracking in such circumstances is to determine how a subject's eyes interact with real-world objects (e.g., other automobiles, products on a store shelf, etc.) In such cases, then, it is desirable to provide the subject with as unobstructed a view of the real-world scene as possible, while still monitoring the ocular object being observed. Thus, it is desirable to preserve an unobstructed and undistorted view path 240 from a real world object space to a subject's eye. In certain optional embodiments, this is accomplished by providing a corrective optical element 235. Corrective optical element 235 is arranged and configured to eliminate any wedge or other optical aberration introduced by looking through prism 215 along viewing path 240. In the case of FIG. 2, where prism 215 is a three sided (in cross section) planar prism, this is accomplished by providing a complementary prism as element 235 in close proximity to prism 215. In particular, element 235 includes a first surface 236 and a second surface 237. First surface 236 is arranged proximate to second surface 217 of first prism 215, and second surface 237 is arranged to be parallel to first surface 216 of prism 215, such that when the subject looks through prism 215 and corrective element 235, the user is effectively looking through a plane parallel plate. In a preferred embodiment corrective element 235 is cemented to, or is otherwise in optical contact with prism 215. In one embodiment, both first prism 215 and corrective element 235 are made of acrylic and the cemented resulting thin plate has a thickness of 5.5 mm.

Figure 3:
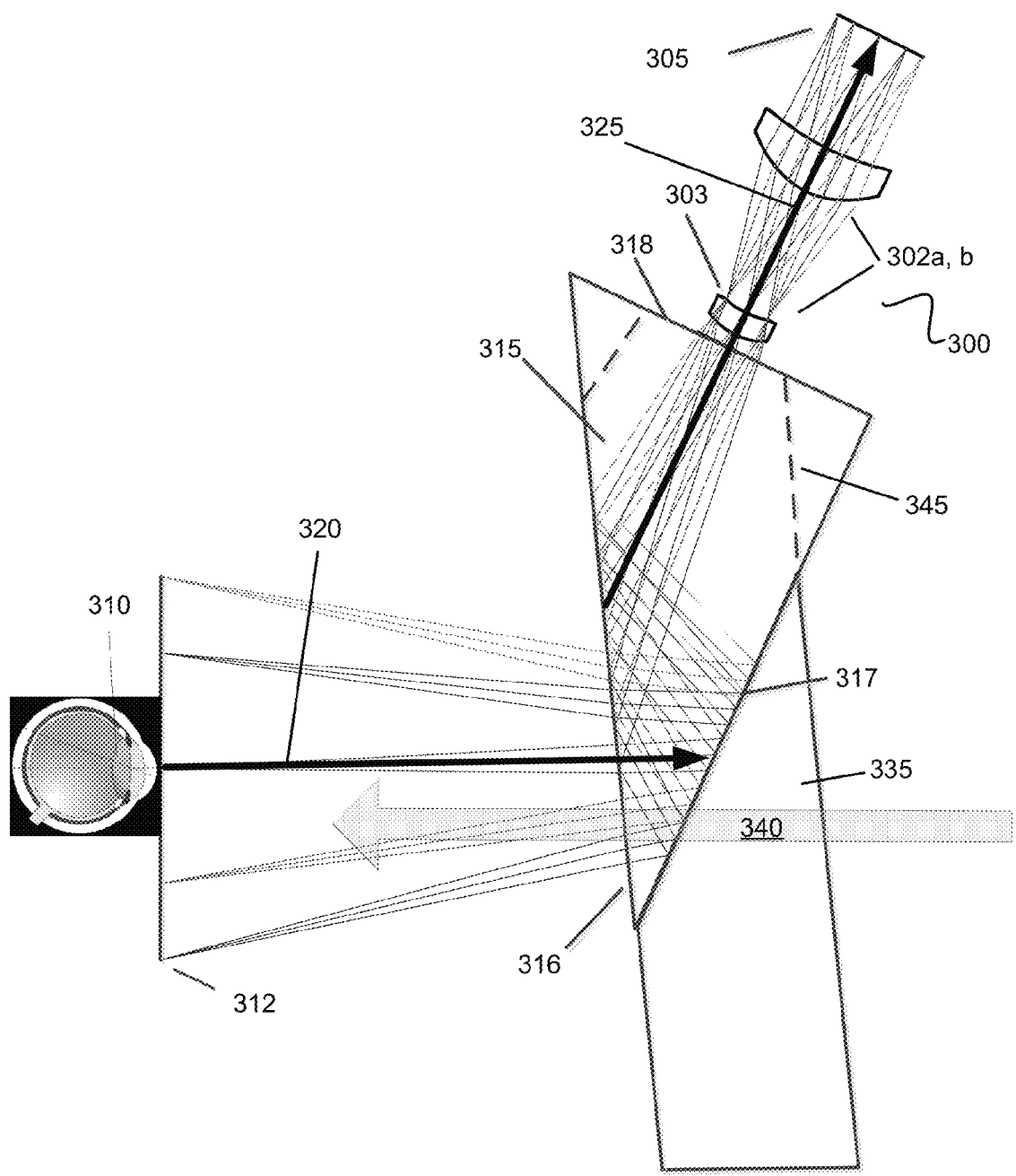
FIG. 3 is a schematic illustration of an eye tracking system according to an embodiment of the invention using an inclined planar prism and an optional corrective optical element.

As is set forth above, prism 215 in FIG. 2 is arranged and configured such that its first surface 216 is orthogonal to first optical axis 220. However, this is not a requirement. FIG. 3 shows an eye tracking system according to an embodiment of the invention in which a first surface 316 is inclined at an angle with respect to first optical axis 320.

As in the system of FIG. 2, the system of FIG. 3 includes an imaging system 300, including lenses 302a, b, and stop 303. As in the system of FIG. 2, additional lenses or other optical elements may be added as necessary for aberration control or other purposes. The system of FIG. 3 also includes sensor 305. Imaging system 300 images an ocular object located at or near eye 310 onto sensor 305.

As in the system of FIG. 3, as light from eye 310 is imaged, it travels through prism 315, where it is folded twice such that a first or original optical axis 320 is folded and translated to a second optical axis 325 along which sensor 305 and the elements of imaging system 300 are arranged. Prism 315 includes a first, second and third surfaces 316, 317, 318. Surface 317 includes an infrared high reflectivity coating, such that infrared light entering first surface 316 is reflected toward second surface 316. At internal side of the surface 316, the light reflects, either through TIR, or through a selectively applied infrared high reflectivity coating covering only the upper part of surface 316 such that the coating does not occlude the original light path into the prism through the first surface 316. After reflection from surface 317, light exits the prism 315 at third surface 318, where it is imaged by imaging system 300 onto sensor 305.

As in the system of FIG. 2, superfluous regions 345 of prism 315 may be trimmed or omitted. Additionally, to compensate for the wedge presented to the subject when looking through prism 315, the system of FIG. 3 may include an optional corrective optical element 335, which together with prism 315, forms a plane parallel plate with respect to the subject's eye 310 along a see-through direction 340.

Figure 4:
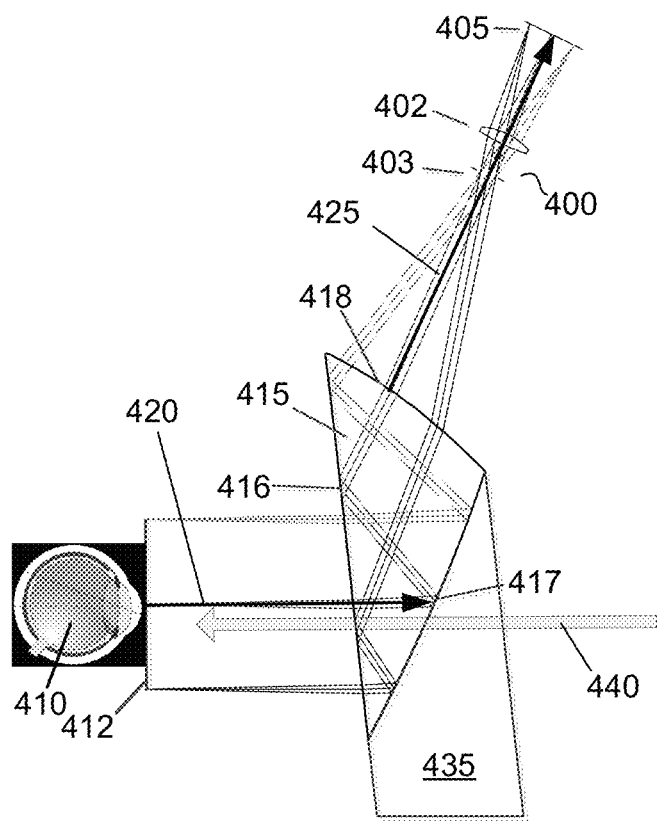
FIG. 4 is a schematic illustration of an eye tracking system according to an embodiment of the invention using a freeform prism and an optional corrective optical element.

FIG. 4 shows a compact eye tracker using a freeform prism. Unlike the systems of FIGS. 2 and 3, which use planar surfaces, the surfaces of prism 415 (surfaces 416, 417 and 418) are so-called "freeform" surfaces, in that their surface figure can be arbitrarily defined by design. For example, surfaces 416, 417 and 418 can be an aspherical, an anamorphic aspherical, an xyp polynomial aspherical, or other types of freeform surfaces. The use of freeform surfaces enables the reduction of the number of lenses in imaging system 400, which in the case of the embodiment of FIG. 4, is a single lens 402, stop 403, and powered freeform surfaces 416, 417, 418. Additional aberration control is accomplished in the embodiment of FIG. 4 by restricting the field over which the imaging system 400 must perform. In addition to providing focusing power and aberration control, surfaces 416, 417 and 418 operate as corresponding surfaces described above with respect to prisms 215 and 315. Light enters surface 416 from eye 410 and reflects from surface 417, which carries a high reflectivity coating optimized for the near infrared. Light then reflects from surface 416 through total internal reflection. The system of FIG. 4 also optionally includes corrective optical element 435 to provide power, wedge and aberration free viewing along view path 440.

In the system of FIG. 4, as in certain other embodiments when a freeform prism's first surface 416 is non-planar, corrective optical element 435 may be designed such that any ray traced from the pupil of eye 410, which will refract upon entering prism 415 at first surface 416, has that refraction effectively cancelled upon exiting a second surface of corrective element 435. In other words, the surface figure of element 435 is designed such that there is no net change in angle from rays traced from pupil to the real world object space beyond the system, although such rays may be axially displaced because of the presence of the dense optical medium of elements 415 and 435 between the eye and real world object space. Such a design has the effect of creating no net change in angle of rays propagating to eye 410 along real world viewing path 440.

Figure 5:
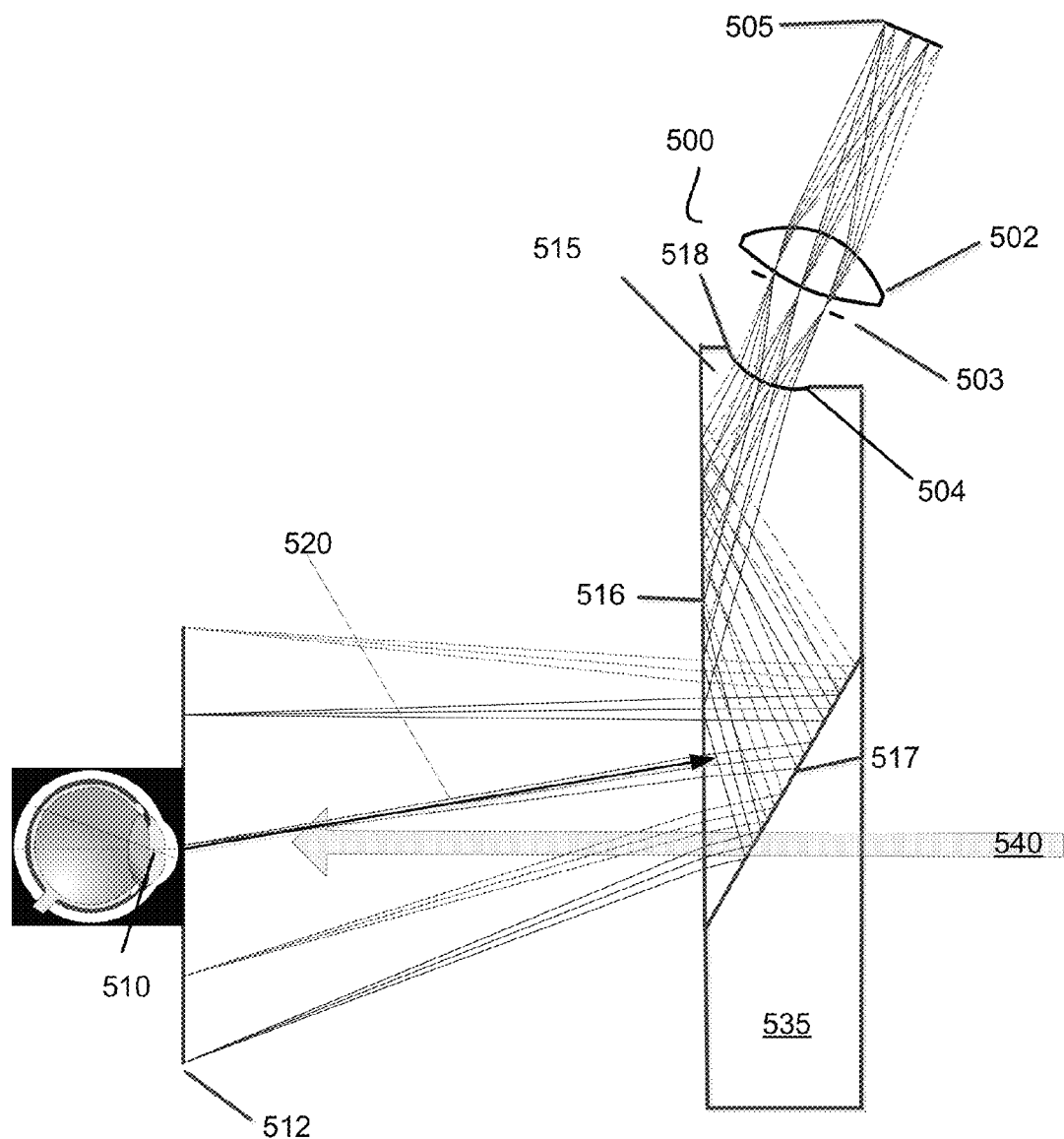
FIG. 5 is a schematic illustration of an eye tracking system according to an embodiment of the invention using a freeform prism having a planar first surface, a powered third surface, and an optional corrective optical element.

Referring now to FIG. 5, a light guiding prism 515 may be provided in which all surfaces but the third surface 518 is planar. Third surface 518 is a freeform surface i.e., an aspherical, an anamorphic aspherical, an xyp polynomial aspherical, or some other type of freeform surface. As in the system of FIG. 4, the use of freeform surface 518 enables a reduction in the number of elements in imaging system 500, which in the case of the system of FIG. 5, includes lens 502, stop 503 and freeform refractive surface 518. Lens 502 may be an asphere to provide additional aberration correction as well as focusing power. As in the systems described above, the prism 515 of the system of FIG. 5 has a second surface 517 with a high reflectivity IR coating, and a first surface 516, which directs light from eye 510, through prism 515 to imaging system 505 by TIR, or a selectively applied infrared high reflectivity coating. The system of FIG. 5 also includes an optional corrective optical element 535, which provides a distortion free viewing path 540 for the subject.

In this embodiment, the optical axis 520 is inclined at an angle with respect to object plane 512 of the eye 510, as compared with the system of FIG. 2 where optical axis 220 is orthogonal to the object plane 212. The tilt of the optical axis 520 introduces a modest amount of keystone distortion into the system of FIG. 5, which can be compensated in a number of ways, for example, by tilting sensor 505, or by designing imaging system 500 with sufficiently large depth of focus/depth of field.

Figure 6:
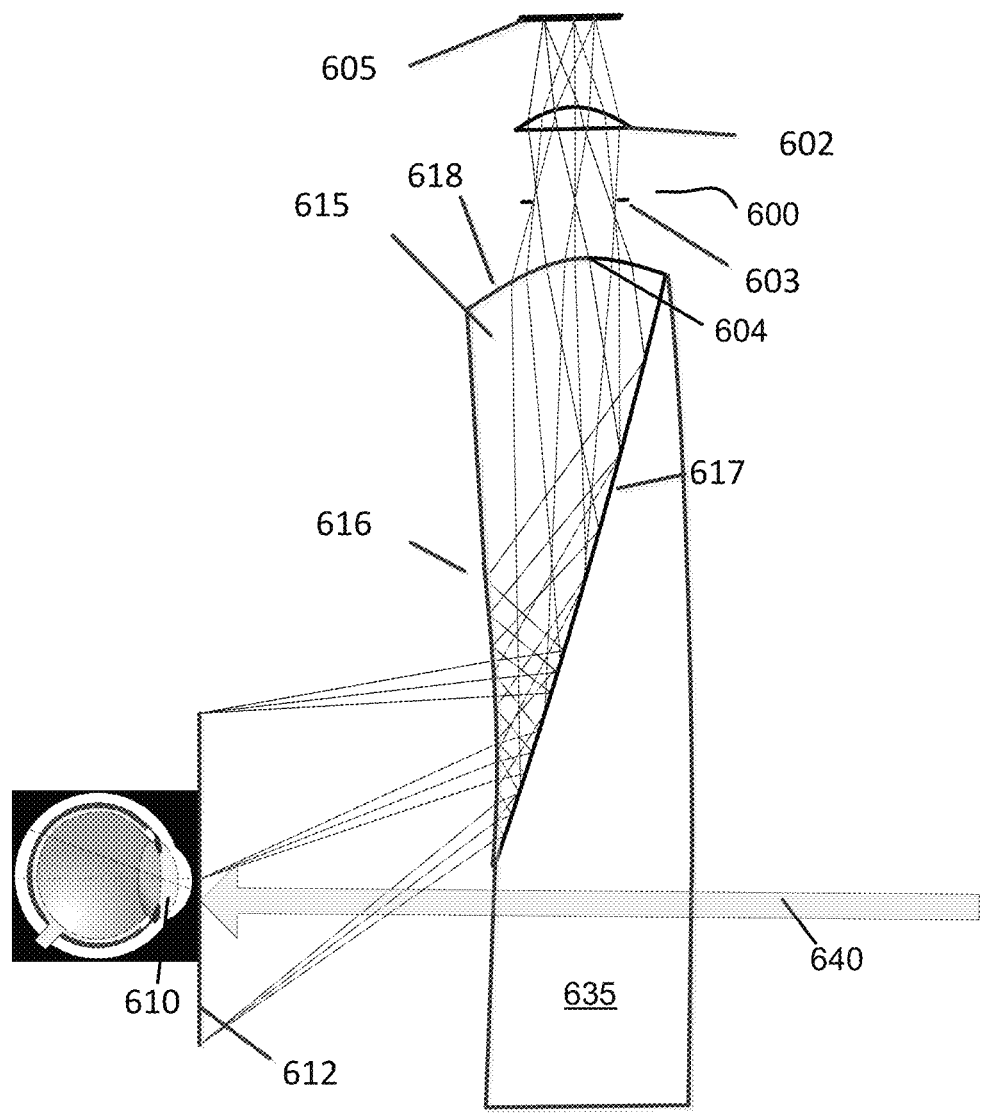
FIG. 6 is a schematic illustration of an eye tracking system according to an embodiment of the invention using a freeform prism supporting three internal reflections and an optional corrective optical element.

Referring now to FIG. 6, there is shown an eye tracking system using a freeform prism 615 in which all of the refractive and reflective surfaces 616, 617, 618 are freeform surfaces, which could be an aspherical, an anamorphic aspherical, an xyp polynomial aspherical, or other types of freeform surfaces. As in previously described embodiments, the prism performs as a light guiding device as well as an image forming device. In the embodiment of FIG. 6, rays originating in an object plane 612 (e.g., at eye 610) centered on a first optical axis pass through prism 615's first surface (616), and are then reflected three times inside the prism by surfaces 617, 616, and again by surface 617. The first reflection from surface 617 is assisted with a highly reflective coating on that surface; however, this coating need not be continuous as reflections from the region of surface 617 nearest to the imaging system 600 will occur by TIR. The intermediate reflection from the first surface occurs through TIR. After multiple reflections, light from the eye 610 exits the prism at refractive surface 618. Imaging system 600 then collects the rays and forms an image at sensor 605. In the system of FIG. 6, the imaging system is realized by all of prism 615's freeform surfaces plus aspheric lens 602 and stop 603. As in previously described embodiments, in order to enable the see-through capability, a freeform corrective optical element 635 is cemented with the freeform prism 615 to correct the viewing axis deviation and undesirable aberrations introduced by the prism to the real world scene. The freeform prism itself is trimmed to a thin profile to reduce weight as shown in embodiment described above.

Figure 7:
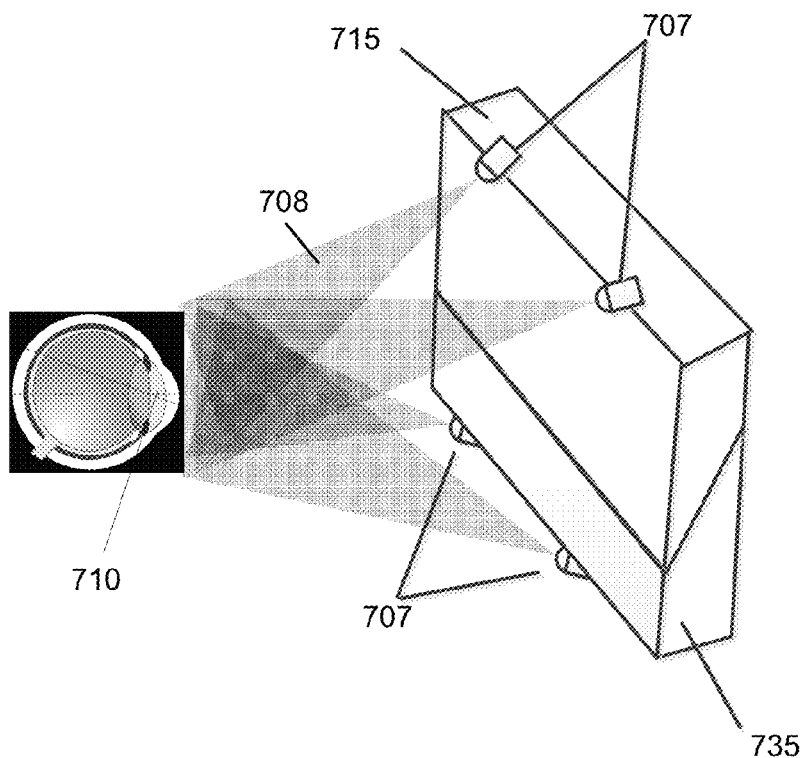
FIG. 7 is a schematic illustration of a variety of illumination arrangements according to embodiments of the invention.
Figure 7:
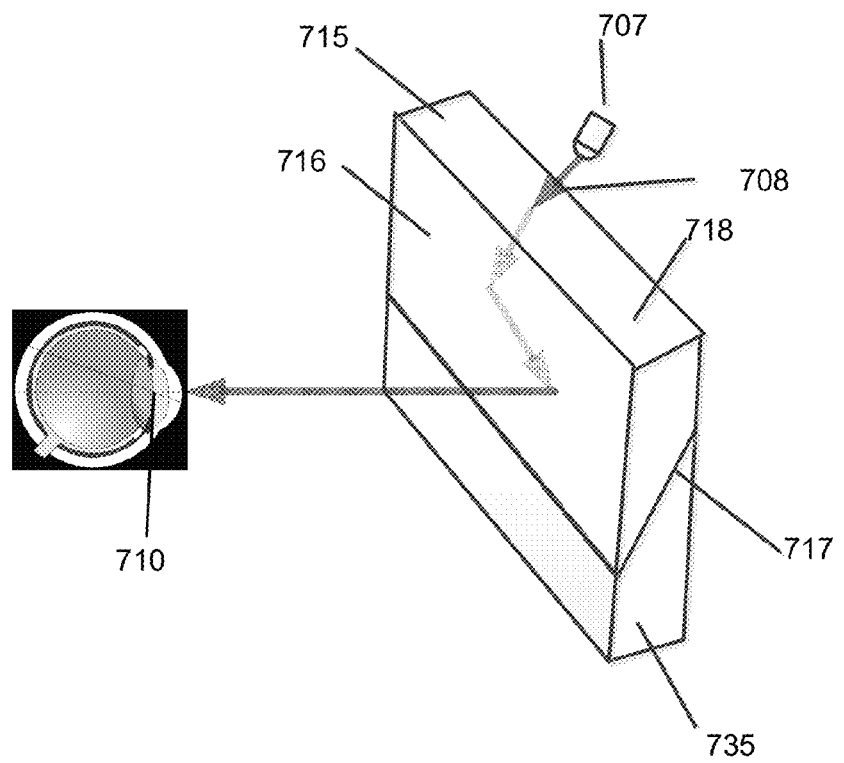

Referring now to FIG. 7, there is shown a variety of illumination arrangements usable in conjunction with the various embodiments of the invention described above. FIG. 7a shows an off-axis illumination arrangement, whereby a plurality of lensed infrared LEDs 707 are arranged around a prism assembly, which itself includes a prism 715 and a corrective optical element 735. LEDs 707 provide off axis illumination 708 to eye 710, which results in the formation of a darkened pupil image.

FIG. 7b shows an on-axis illumination arrangement. In the arrangement of FIG. 7b, one or more light sources 707 is placed near the imaging system components such that light is directed along the same optical path as imaging light, but in the opposite direction. In a preferred embodiment, light sources 707 are located near the aperture stop used in the imaging system, and the beams 708 generated by light sources 707 are directed along the second optical axis described above with respect to FIG. 1. In the arrangement of FIG. 7b, illumination light enters prism 715 through third surface 718, and reflects off first surface 716, for example, by TIR. Illumination light then reflects off second surface 717, exits prism 715 at first surface 716 along the first optical axis in the direction of eye 710. On axis-illumination supplied in this manner creates an image of a bright pupil. As in the embodiments described above, second surface 717 may include a high reflectivity IR coating.

Figure 8:
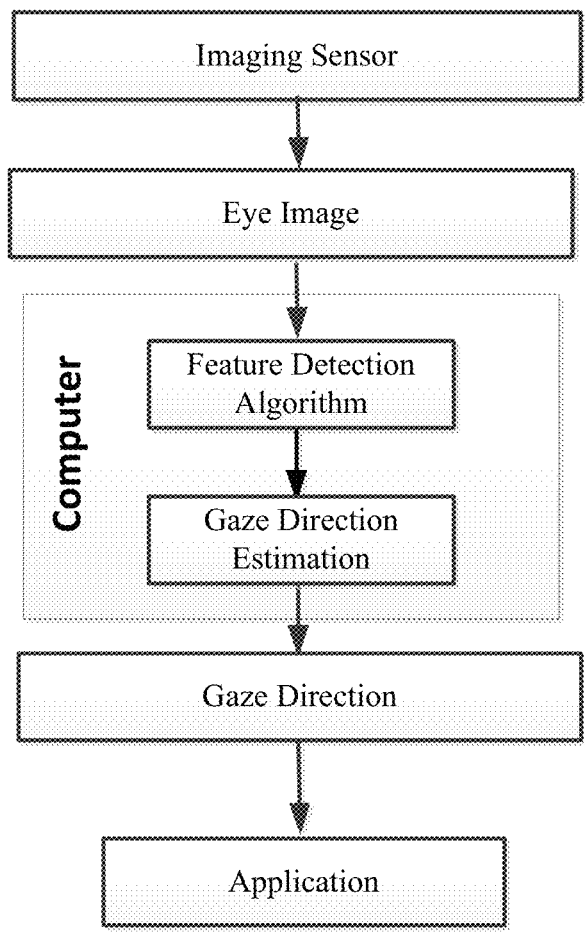
FIG. 8 is a block diagram showing an exemplary image processing method in accordance with an embodiment of the invention.

FIG. 8 shows an exemplary image processing process in accordance with an embodiment of the invention. According to the method of FIG. 8, an imaging sensor receives an image of an ocular object. The sensor translates the optical image into an electrical signal generating image data, which is received by a computer having a programmable processor in communication with electronic storage (i.e., a non-transitory computer readable medium having computer executable instructions). The computer applies one or more feature detection algorithms to the image data received from the sensor, to detect ocular features. The computer then calculates the gaze direction of the subject's eye on the basis of the detected ocular feature. The computer then provides the calculated gaze direction to an application.

While the preferred embodiments of the present invention have been illustrated in detail, it should be apparent that modifications and adaptations to those embodiments may occur to one skilled in the art without departing from the scope of the present invention as set forth in the following claims.

What is claimed is:

1. An optical system for eye tracking, comprising:
a prism having a first, second and third surface, the prism having a first optical axis intersecting the first surface, and a second optical axis intersecting and approximately orthogonal to the third surface;
an imaging system and a sensor arranged along the second optical axis,
wherein, the prism is configured such that an ocular object positioned about the first optical axis is imaged by the imaging system onto the sensor through the prism;
wherein the prism is configured such that light from an ocular object positioned about the first optical axis enters the prism at the first surface and exits the prism through the third surface prior to being imaged by the imaging system onto the sensor;
wherein the prism is configured such that light from an ocular object positioned about the first optical axis entering the prism along the first axis reflects off an interior side of the second surface and reflects off an interior side of the first surface before exiting the prism through the third surface,
wherein the first surface is an exterior surface that includes a highly reflective coating for light within a predetermined wavelength range incident on an interior side of the first surface,
and further comprising a corrective optical element arranged along the first optical axis, wherein the corrective optical element has a first surface adjacent to the second surface of the prism, and a second surface, and wherein the corrective optical element is arranged such the corrective optical element counteracts any visual distortion introduced by the prism when looking through the prism and the corrective optical element along the first optical axis.

2. The optical system of claim 1, wherein the prism is configured such that light propagating along the first optical axis that enters the prism at the first surface reflects at least twice within the prism to exit the third surface along the second optical axis.

3. The optical system of claim 1, wherein the prism is configured such that at least a portion of the reflection off the interior side of the first surface occurs by total internal reflection.

4. The optical system of claim 1, wherein the reflective coating extends over only a portion of the first surface.

5. The optical system of claim 1, wherein the highly reflective coating comprises a dielectric thin film stack having high reflectivity for near infrared light.

6. The optical system of claim 1, wherein the prism is configured such that light from an ocular object positioned about the first optical axis entering the prism along the first axis reflects off an interior side of the second surface, reflects off an interior side of the first surface, and again reflects off an interior side of the second surface before exiting the prism through the third surface.

7. The optical system of claim 1, wherein the second surface includes a coating having high reflectivity for light within a predetermined wavelength range incident on the interior side of the second surface.

8. The optical system of claim 7, wherein the predetermined wavelength range is between about 700 nm and 1.5 um.

9. The optical system of claim 7, wherein the coating comprises a dielectric thin film stack having of high reflectivity for near infrared light.

10. The optical system of claim 1, wherein the imaging system comprises a first lens, a second lens, and a stop located between the first and second lenses.

11. The optical system of claim 1, wherein at least one of the first, second or third surfaces is a freeform surface.

12. The optical system of claim 1, wherein at least one of the first, second or third surfaces has optical power.

* * * * *